(12) United States Patent
Mian et al.

(10) Patent No.: US 6,523,411 B1
(45) Date of Patent: Feb. 25, 2003

(54) WHEEL INSPECTION SYSTEM

(75) Inventors: Zahid F. Mian, Loudonville, NY (US);
William Peabody, Saratoga Springs, NY (US); Theodore Haller, Scotia, NY (US)

(73) Assignee: International Electronic Machines Corp., Albany, NY (US)

( * ) Notice: Subject to any disclaimer, the term of this patent is extended or adjusted under 35 U.S.C. 154(b) by 0 days.

(21) Appl. No.: 09/532,137

(22) Filed: Mar. 21, 2000

(51) Int. Cl.$^7$ .............................................. G01N 29/04
(52) U.S. Cl. .............................. 73/620; 73/602; 73/639
(58) Field of Search ........................... 73/636, 635, 632, 73/602, 618, 620, 627, 628, 633, 640, 641, 643, 634, 637, 638, 639; 702/35, 38, 39

(56) References Cited

U.S. PATENT DOCUMENTS

| 3,812,708 A | 5/1974 | Cowan et al. |
| 4,904,939 A | 2/1990 | Mian |
| 5,636,026 A | 6/1997 | Mian et al. |
| 5,814,731 A | * 9/1998 | Alexander et al. ............ 73/644 |

FOREIGN PATENT DOCUMENTS

| DE | 32 18 453 A1 | 5/1982 |
| DE | 35 05 280 A1 | 2/1985 |

OTHER PUBLICATIONS

"WheelCracks? WheelFacts? WheelFAX!" brochure, Scanning Systems, Inc., Jan. 1974.
"IEM Wheel Inspection Station" brochure, International Electronic Machines, Inc., Nov. 1998.
"Report No. 22 Tread Crack Detection In Railroad Wheels: An Ultrasonic System Using EMATs," National Institute of Standards and Technology, May 1991.

* cited by examiner

Primary Examiner—Richard A. Moller
(74) Attorney, Agent, or Firm—Hoffman, Warnick & D'Alessandro LLC; Spencer K. Warnick

(57) ABSTRACT

A wheel inspection system based on electromagnetic acoustic signals and having improved inspection by the use of a noise removing system and/or a pivotal mounting system. The invention also includes an improved detection head and data analysis.

24 Claims, 12 Drawing Sheets

WHEEL INSPECTION SYSTEM

BACKGROUND OF THE INVENTION

1. Technical Field

The present invention relates generally to detection of defects in railroad wheels. More particularly, this invention relates to improved electromagnetic acoustic testing of wheels for defects.

2. Related Art

In the railroad and related industries, wheel defects and/or extreme wear are a major cause of derailments leading to property loss and loss of life. Detection of defects and wear before a tragedy occurs, therefore, has become indispensable. An ideal device must address the requirements of: longevity, accuracy, reliability, quickness and expense. Unfortunately, no fully satisfactory automated means capable of meeting these requirements for testing railroad wheels on rolling stock presently exists.

U.S. Pat. No. 3,812,708 to Cowan et al. teaches the use of ultrasonic transducers enclosed in a flexible fluid-filled boot and positioned adjacent to a thin vertical rail in a test zone. In this device, the liquid-filled urethane boot suffers from fragility since it is susceptible to small cuts that release the liquid. In addition, the system is inaccurate because it produces a high rate of false positive indications. See also Scanning Systems, Inc. "WheelCracks? Wheelfacts? WheelFAX!" brochure.

German document DE 3218453A1 to Salzberger et al. discloses a device using electromagnetic acoustic transducers (EMATs). This system reduces the number of false positives, but is inflexible because it can only test wheels having tightly controlled wear profiles. This system also suffers from the use of electromagnets, which create an upper limit on train length due to overheating in the transducer. Finally this system is incapable of real time on-line signal processing necessary in heavy traffic situations.

National Institute of Standards and Technology, Report No. 22, Tread Crack Detection in Railroad Wheels: An Ultrasonic System Using EMATs, by Schramm et. al., discloses improvements to the Salzberger et al. device. Shramm et al. introduce membrane sensing switches and conforming transducers to expand wheel profile and size compatibility and suggest improvements in signal processing. As indicated in that document, there are a number of shortcomings of this device. Problems include corrosion and a lack of a workable mounting mechanism for the sensor. Due to a lack of a mounting system, the device requires a lot of attention by a user and is unreliable. It is also expensive to use because the transducer is free to move around and, hence, susceptible to breakage. Another problem with the system is noise created by the traction system of the locomotive, which creates false positive indications.

In view of the foregoing there is a need in the art for a wheel inspection system that exhibits: longevity, accuracy, reliability, quickness, cost-effectiveness and user independence.

SUMMARY OF THE INVENTION

In a first general aspect of the invention is provided a wheel inspection system having: an electromagnetic acoustic transducer having a transmit coil to propagate an ultrasonic wave into a wheel and a receiving coil to receive an ultrasonic surface wave from the wheel; a radio frequency generator for exciting the electromagnetic acoustic transducer and producing an ultrasonic wave in the wheel; a computer control unit connected to and communicating with the radio frequency generator and the electromagnetic acoustic transducer; a data acquisition unit connected to and in communication with the computer control unit and the electromagnetic acoustic transducer assembly for determining defects in the wheel; and a noise removing system to remove noise from the data. This aspect provides a system capable of accurately, quickly and reliably detecting defects in a wheel.

In a second general aspect of the invention is provided A detection head for an electromagnetic acoustic transducer wheel inspection system, the detection head having: a housing for holding transducer components, the detection head including a transducer pocket and a magnet pocket; a removable magnet assembly for removably mounting a magnet to the magnet pocket; and a removable transducer assembly for removably mounting a coil assembly of the transducer to the transducer pocket.

In a third general aspect of the invention is provided a wheel inspection system having a sensor for receiving signals sent through a wheel; and a data acquisition unit connected to and in communication with the sensor, the data acquisition unit including a neural network, to determine the presence of defects in the wheel, for each sensor.

A fourth general aspect of the invention provides a wheel inspection system having means for detecting defects in a wheel; and means for pivotally mounting the detecting means to a wheel supporting surface such that the detecting means may pivot about least two axes.

The foregoing and other features and advantages of the invention will be apparent from the following more particular description of preferred embodiments of the invention.

BRIEF DESCRIPTION OF THE DRAWINGS

The preferred embodiments of this invention will be described in detail, with reference to the following figures, wherein like designations denote like elements, and wherein.

DESCRIPTION OF THE PREFERRED EMBODIMENTS

Although certain preferred embodiments of the present invention will be shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as an example of the preferred embodiment.

For purposes of this disclosure, the term "defect" may refer to any of a variety of shortcomings or faults such as cracks, surface quality and other wheel integrity degradations.

Figure 1A:
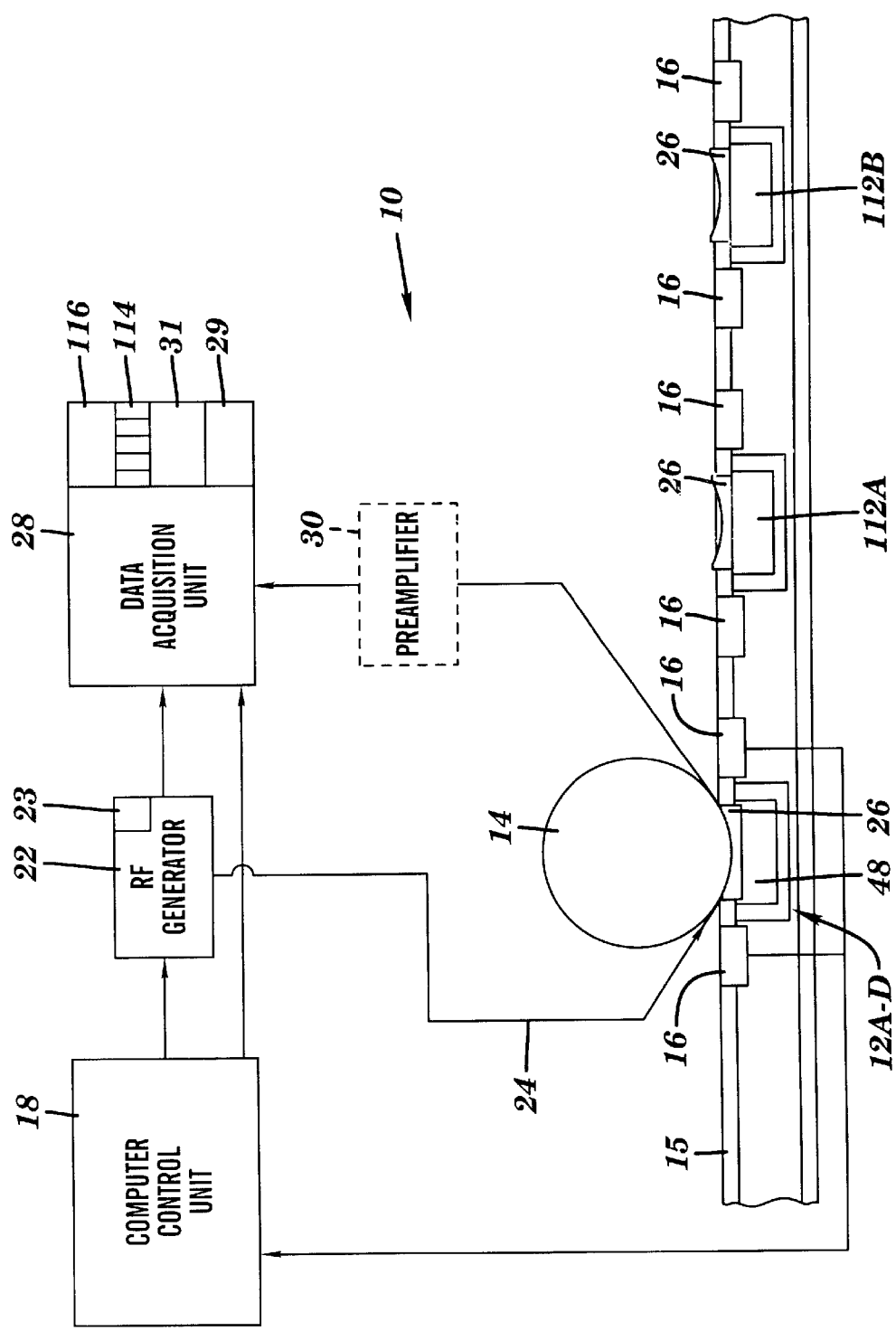
FIG. 1A is a schematic overview of a wheel inspection system in accordance with the invention.

Referring to FIG. 1A, a schematic overview of a wheel inspection system 10 of the invention is illustrated. Wheel inspection system 10 includes at least one wheel defect detector in the form of an electromagnetic acoustic transducer (EMAT) 12A–D. As a wheel 14 to be examined rolls into position on a wheel supporting surface 15, sensors 16 detect wheel position and transmit this information to a computer control unit 18. Sensors 16 may take a variety of forms but are preferably non-contact proximity detectors, e.g., eddy current detectors. Computer control unit 18 activates a radio frequency (RF) generator 22 to produce a series of RF energy pulses that are delivered by cables 24 (preferably co-axial cables) to an acoustic transducer 26 of EMAT 12A–D. A permanent magnet 48 is positioned below acoustic transducer 26. A timing pulse is also transmitted from RF generator 22 to a data acquisition unit 28 to synchronize data acquisition unit 28 with RF generator 22. Also, computer control unit 18 signals data acquisition unit 28 to prepare it to receive data.

As RF energy pulses emit from acoustic transducer 26, eddy currents are created in wheel 14. Simultaneously, permanent magnet 48 creates a magnetic field in wheel 14. The result is a Lorentz force on wheel 14 that creates deformation and ultrasonic traveling waves in wheel 14. The path of the ultrasonic waves may be controlled by where the RF energy pulses are transmitted. RF generator 22 may also produce a plurality of frequency components in an output thereof to create a series of ultrasonic waves that travel in varying depths within wheel 14.

While RF generator 22 preferably outputs power in the kilowatt range, signals received are in the sub-microvolt range and, therefore, are preferably amplified about 70 DB by preamplifier 30. Furthermore, RF generator 22 may include a bridge network 23 to couple multiple radio frequency sources of RF generator 22 to transmit coil 42 to increase the transmitted power.

As reflected and transmitted ultrasound waves are received by transducer 26, they are converted to electrical signals and may be preamplified at preamplifier 30 prior to being sent to data acquisition unit 28 for processing. In data acquisition unit 28 algorithms are employed to extract information concerning defects from the signal data. When RF generator 22 creates a plurality of frequency components, the series of ultrasonic waves that travel in varying depths within wheel 14 can be used to interrogate various volumes of the wheel material to locate any defects internal to wheel 14.

Figure 1B:
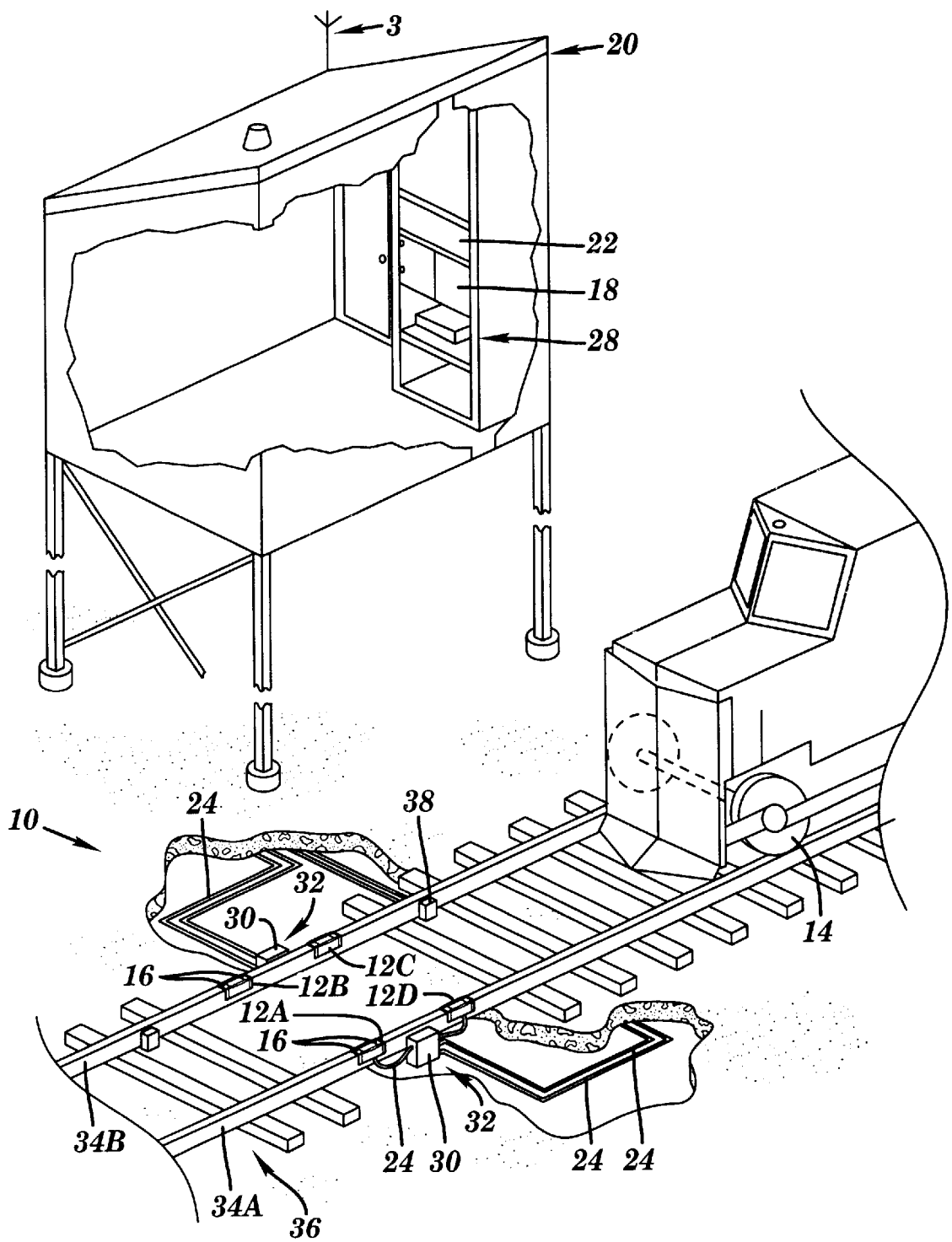
FIG. 1B is a perspective view of the wheel inspection system of FIG. 1A mounted in a rail for testing an approaching wheel.

Referring to FIG. 1B, a preferred embodiment of system 10, in the railroad environment, is shown. EMATs 12A–D are mounted on at least one rail 34A, 34B of a multiple rail track 36 and communicate through cables 24 with computer control unit 18, RF generator 22, preamplifier 30 and data acquisition unit 28. Preferably, most of these electric components reside in a field side shed 20. However, field side electronics 32 including, for example, pre-amplifiers 30 and filters may also be mounted on rail(s) 34A, 34B. Approach sensors 38 are provided to signal approach of an approaching wheeled vehicle, e.g., locomotive, rail car, etc.

Figure 2:
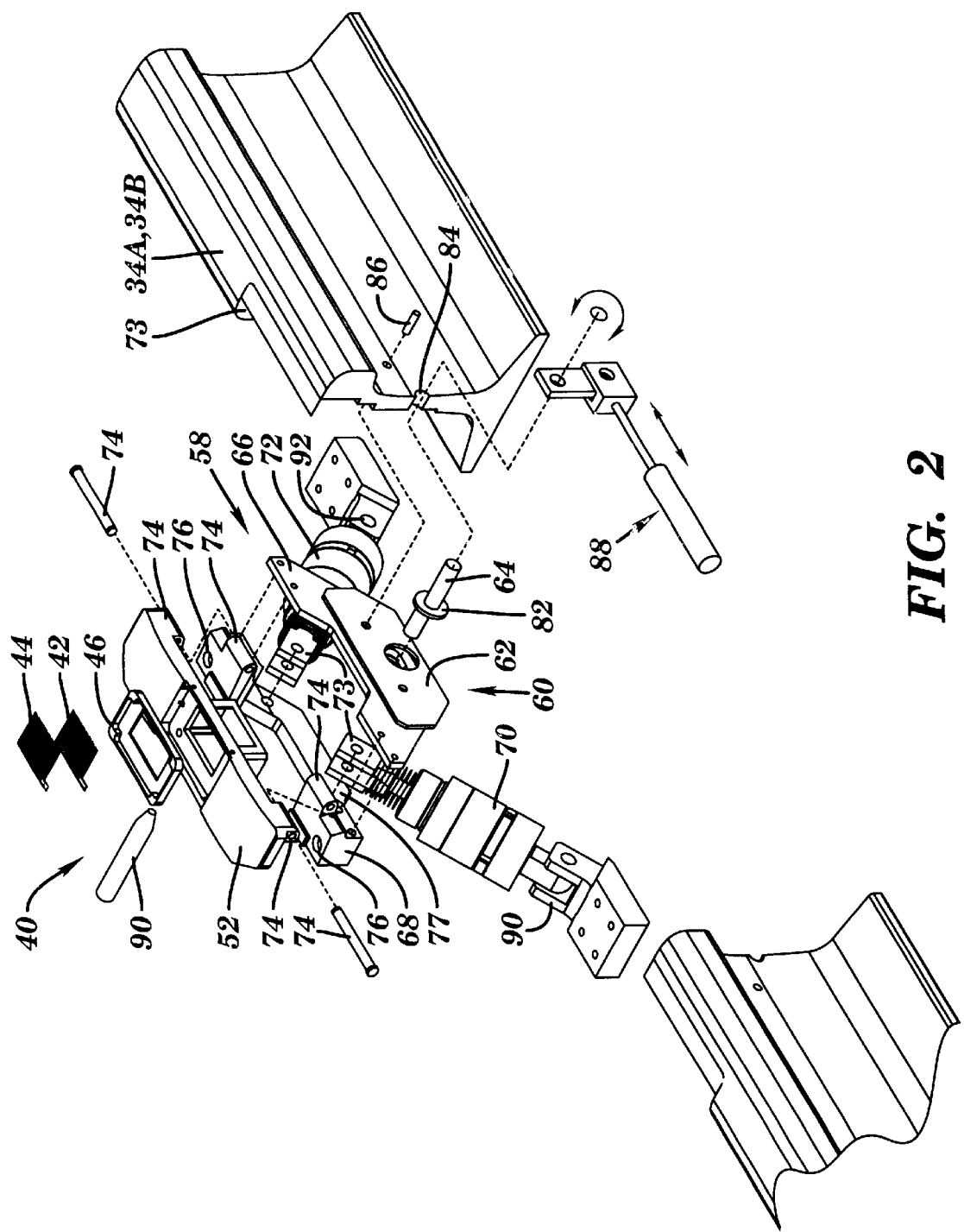
FIG. 2 is an exploded perspective view of a wheel inspection system having a retractable mounting system in accordance with the invention.
Figure 3:
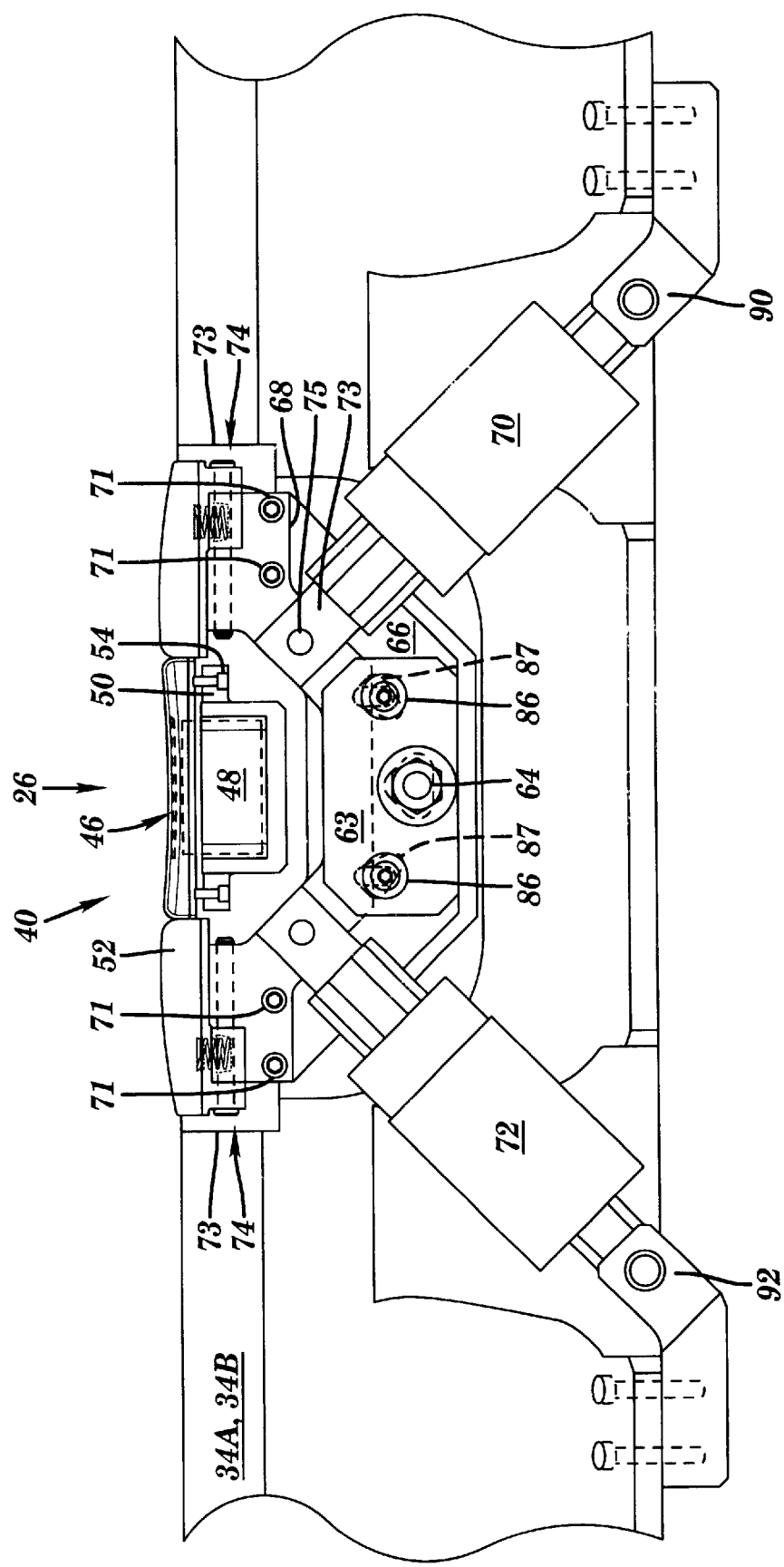
FIG. 3 is a side elevation view of the retractable mounting system of FIG. 2.
Figure 5:
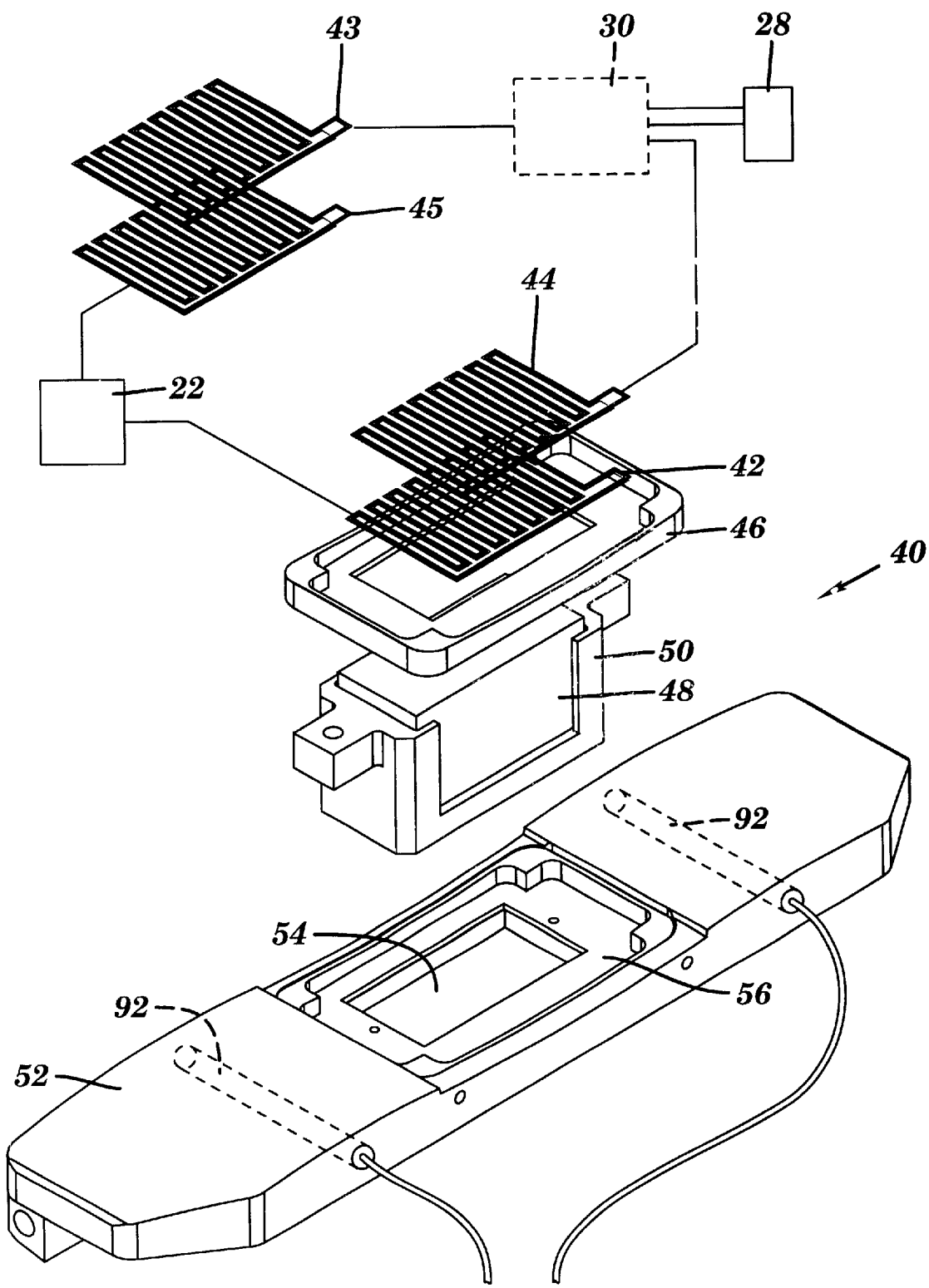
FIG. 5 is an exploded perspective view of a detection head and transducer of the wheel inspection system.

Referring to FIGS. 2, 3 and 5, a preferred embodiment of a detection head 40 for mounting transducer 26 and details of transducer 26 are shown. Transducer 26 includes at least one transmit coil 42 and at least one receiving coil 44. Detection head 40 includes: transducer 26, a removable transducer assembly 46, a permanent magnet 48, a removable magnet assembly 50 and a detection head housing 52.

With regard to transducer 26, shown in FIG. 5, transmit coil 42 is connected to RF generator 22. Overlying transmit coil 42 is at least one receiving coil 44 whose output may communicate with pre-amplifier 30 or directly with data acquisition unit 28. Electrical connections to coils 42, 44 are routed in an appropriate manner through detection head housing 52 to a junction at which a cable 24 can interconnect to electronics 32 located in proximity to detection head 40. Both transmit coil 42 and receiving coil 44 are preferably serpentine in shape and are preferably physically offset relative to one another to prevent overlap of coils and interference therebetween. It is also possible to provide a plurality of receiving coils 43, 44 and transmit coils 42, 45 of differing configurations to transmit and receive ultrasonic waves that penetrate different portions of wheel 14. For instance, a first ultrasonic wave traveling substantially at a tread surface of wheel 14 and a second ultrasonic wave traveling substantially at a flange surface of wheel 14, can be received to inspect for particular defects. Otherwise, the length and number of coils 42–45 are chosen to correspond to an ultrasonic wavelength of the desired operating frequency. Of note, although the vertical position of the coils is shown to be alternating between transmit and receiving coils, the vertical position of the types of coils may vary.

Coils 42–45 are mounted on flexible material such as polymeric composite. Removable transducer assembly 46 may also be made of a flexible material such as plastic. As a result, coils 42–45 along with removable transducer assembly 46 are capable of bending to a limited degree. This flexibility allows coils 42–45 to conform to a contour of a wheel 14, as shown in FIG. 1A, and allows for more, and more accurate, data frames to be obtained in a single pass.

With regard to detection head 40, as shown in FIGS. 3 and 5, permanent magnet 48 is supported by removable magnet assembly 50 and coils 42–45 are supported by removable transducer assembly 46. Detection head housing 52 includes a magnet pocket 54 to which removable magnet assembly 50 is removably fixed. As will be described below in more detail, magnet assembly 50 is preferably retractably mounted to an underside of housing 52. Detection head housing 52 also includes a transducer pocket 56 to which removable transducer assembly 46 is removably fixed. Providing permanent magnet 48 and coils 42–45 in removable assemblies is advantageous, e.g., for quick and easy replacement of parts.

FIGS. 2 and 3 show a mounting system 58 for pivotally mounting detection head 40 for pivoting in at least two directions. Mounting system 58 is also retractable. A function of system 58, inter alia, is to reliably support detection head 40, including transducer 26, while allowing translation and rotation with passage of wheel 14 so, along with the flexibility of coils 42–45, maximum contact time with wheel 14 is obtained. Mounting system 58 provides this by allowing pivoting of detection head 40 about a first axis parallel to a wheel axis and about a second axis perpendicular to the first axis. Longer contact time allows for more accurate data frames to be received and improved quality of statistical averaging of resulting signals. Retractable mounting system 58 is preferably positioned in a machined out region 73 of rail 34A, 34b.

In a preferred embodiment shown in FIGS. 2 and 3, retractable mounting system 58 includes a pivot assembly 60 having a bearing plate 62, an eccentric cam bolt 64, a pivot plate 66, a head mounting frame 68, a first shock absorber 70 and a second shock absorber 72.

Head mounting frame 68 of pivot assembly 60 includes a hinge connection 74 to detection head housing 52 and apertures 76 for receiving compression springs (not shown) to control pivoting about hinge connection 74. Hinge connection 74 allows pivoting of detection head housing 52 about an axis substantially perpendicular to a wheel axis, or substantially parallel to rail 34A, 34B. Head mounting frame 68 is also pivotally mounted to pivot plate 66 by appropriate fasteners 71. At a protruding portion 77 of head mounting frame 68, first and second shock absorbers 70, 72 are attached by appropriate structure, e.g., clevis 73 and fasteners 75.

Figure 4:
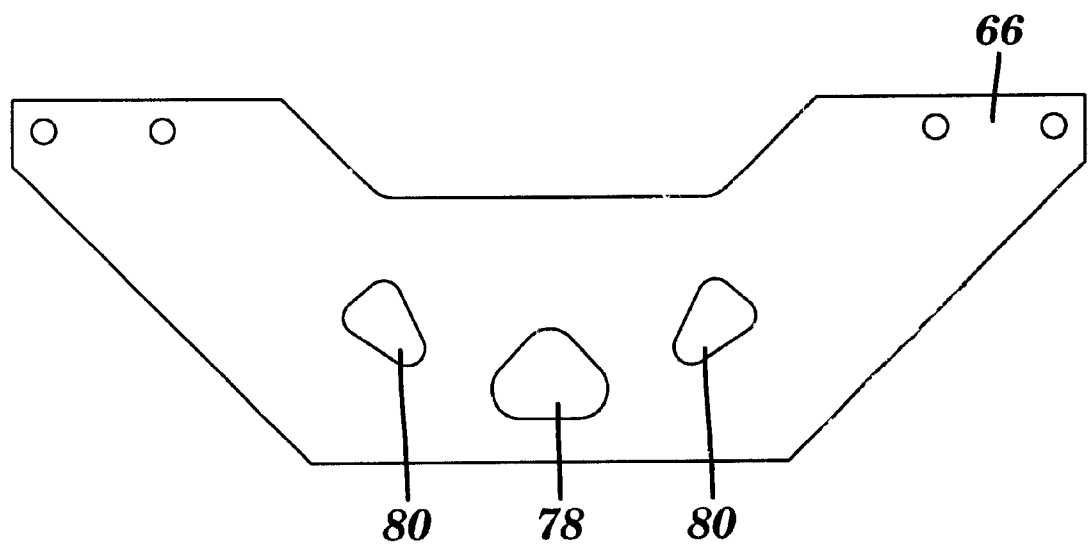
FIG. 4 is a side elevation view of a pivot plate of the retractable mounting system.

As shown in FIG. 4, pivot plate 66 of pivot assembly 60 preferably includes a central substantially triangular opening 78 and a pair of side substantially triangular openings 80. Central opening 78 receives therein a cam portion 82 of eccentric cam bolt 64. An end of eccentric cam bolt 60 is rotatably mounted in an aperture 84 extending through one of rails 34A, 34B. Studs 86 also extend through apertures in rail 34A, 34B and bearing plate 62 and through side openings 80 in pivot plate 66. Appropriate retaining devices 87 are provided on opposite ends of studs 86 to hold the system together. As seen in FIG. 3, a second bearing plate 63 may also be provided on the opposite side of pivot plate 66.

In operation, rotation of eccentric cam bolt 64, via cam portion 82 interacting with central opening 78, controls the height at which pivot plate 66 and, accordingly, mounting frame 68 and detection head 40 sit relative to the top of a rail 34A, 34B. Rotation of cam bolt 64, hence, moves detection head 40 between an operative position adjacent a top surface of a rail 34A, 34B and an inoperative, retracted position. Rotation of eccentric cam bolt 64 is controlled by an actuator and clevis system 88 coupled to the end of cam bolt 64 extending through a rail 34A, 34B. The actuator may be any type commonly used in the industry such as an air or hydraulic cylinder.

Studs 86, which extend through rail 34A, 34B, bearing plate 62 and side openings 80, limit the amount of pivoting allowed in detection head 40 about a first axis parallel to a wheel axis. Further limiting and controlling pivoting about that axis are first and second shock absorbers 70, 72. Shock absorbers 70, 72 are coupled to mounting frame 68 and, at opposite ends 90, 92, respectively, to a rail 34A, 34B or adjacent rail ties. First and second shock absorbers 70, 72 are preferably fluid-filled members. However, other structures capable of absorbing movement of system 58, e.g., compression springs, will be recognizable to those with ordinary skill in the art.

Bearing plate(s) 62, 63 is preferably made of low friction material, such as nickel or a polymeric material, which allows a sliding action with pivot plate 66. The movement of retractable mounting system 58 can be described as an arc whose center point is perpendicular to a longitudinal axis of rail 34A, 34B.

Pivot assembly 60, hence, allows controlled pivoting movement of detection head 40 about a first axis parallel to a wheel axis and a second axis substantially perpendicular thereto.

As shown in FIG. 2, the preferred embodiment of system 58 may also include an air blast nozzle 90 mounted adjacent detection head 40 for dislodging any accumulated debris from the active surface of transducer 26. Furthermore, as shown in FIG. 5, detection head housing 52 may include electric resistance heating elements 92 for controlling the temperature of detection head 40. Temperature control is advantageous, for example, to unfreeze any accumulated cold weather debris, such as ice. This allows operation of the system in many different environments.

Figure 6A:
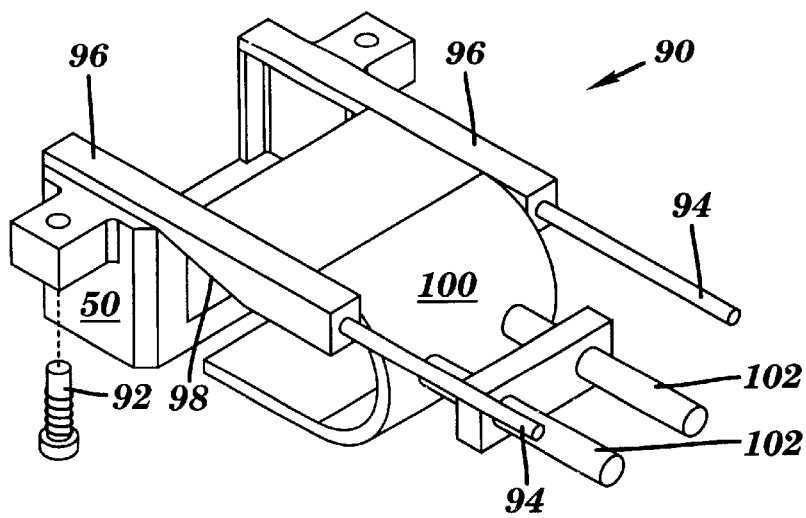
FIGS. 6A–C are perspective views of a magnet flux diversion cover for the wheel inspection system.
Figure 6B:
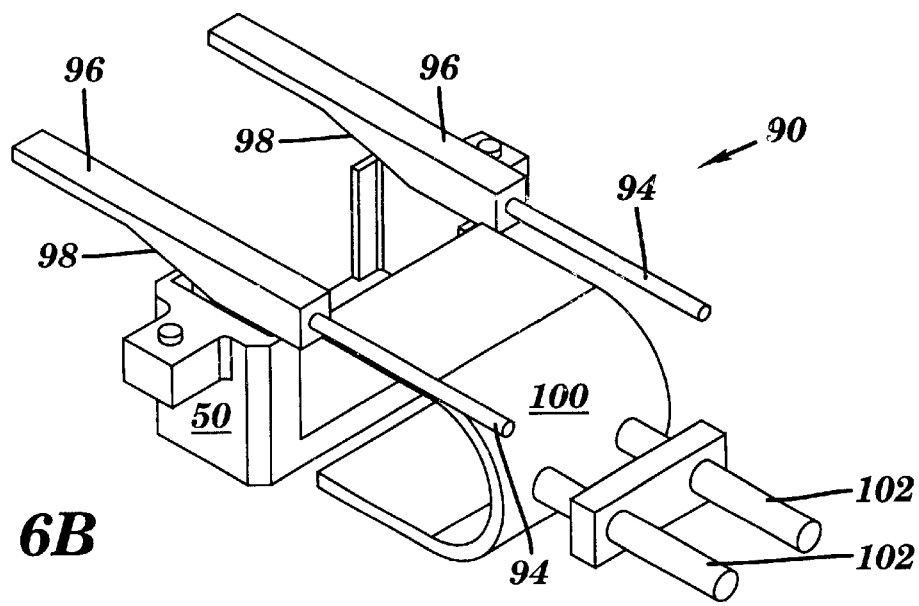
Figure 6C:
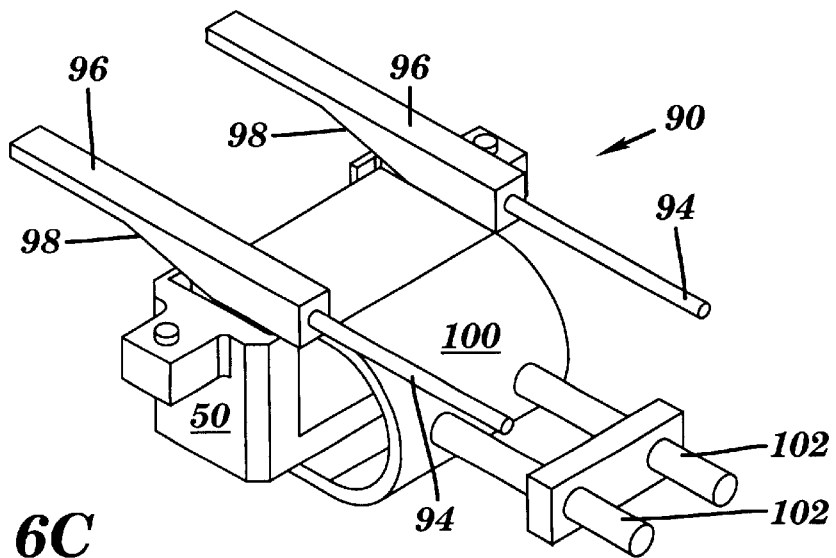

Referring to FIGS. 6A–C, an alternative magnet flux diversion cover 90 for detection head 40 is shown. Magnet flux cover 90 includes magnet assembly retraction actuator(s) 94, retraction guide rail(s) 96, a magnetic flux diverter 100 and diverter cover actuator(s) 102. Referencing FIGS. 5 and 6A, removable magnet assembly 50 is mounted to an underside of detection head housing 52 by biasing fasteners 92, one shown in FIG. 6A, such as a bolt and interposed spring, that biases magnet assembly 50 to the underside of housing 52. Magnet flux diversion cover 90 is mounted adjacent to housing 52.

Diversion cover 90 includes at least one and preferably a pair of magnet assembly retraction actuators 94 having at an end thereof retraction guide rail(s) 96. Each retraction guide rail 96 is interposed housing 52 and magnet assembly 50. Each retraction guide rail 96 includes a ramped portion 98. As shown in FIG. 6B, when retraction activators 94 are engaged, retraction guide rails 96 act against the bias of biasing fasteners 92 and slide across a top of a magnet assembly 50, moving it away from housing 52. As shown in FIG. 6C, with magnet assembly 50 in a retracted position, a magnetic flux diverter 100 is translated by at least one and preferably a pair of diverter actuators 102 to engage magnet assembly 50. Magnetic flux diverter 100, in this position, covers magnet 48 to reduce the external magnetic field.

Figure 7:
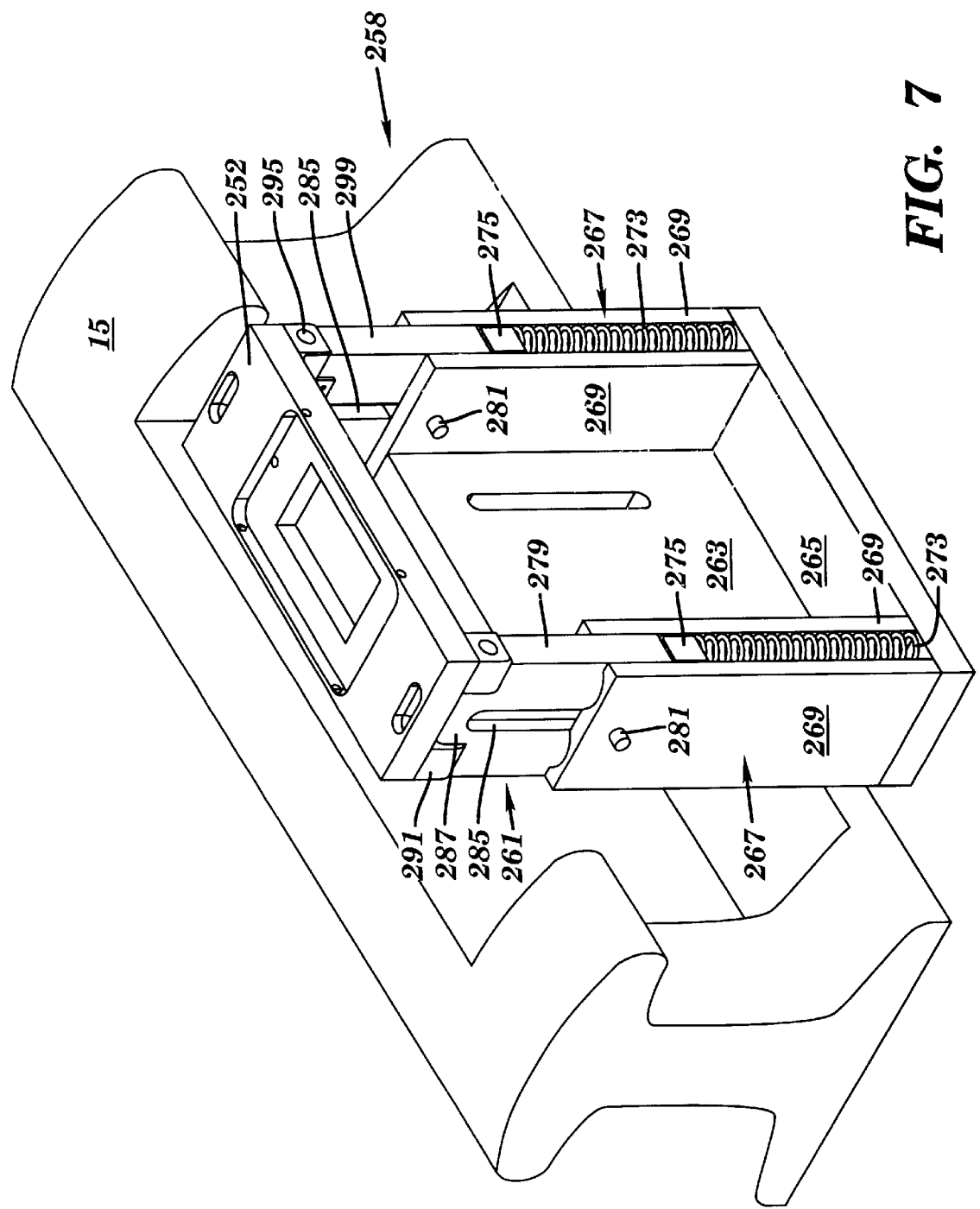
FIG. 7 is a perspective view of an alternative preferred embodiment of the retractable mounting system.
Figure 8:
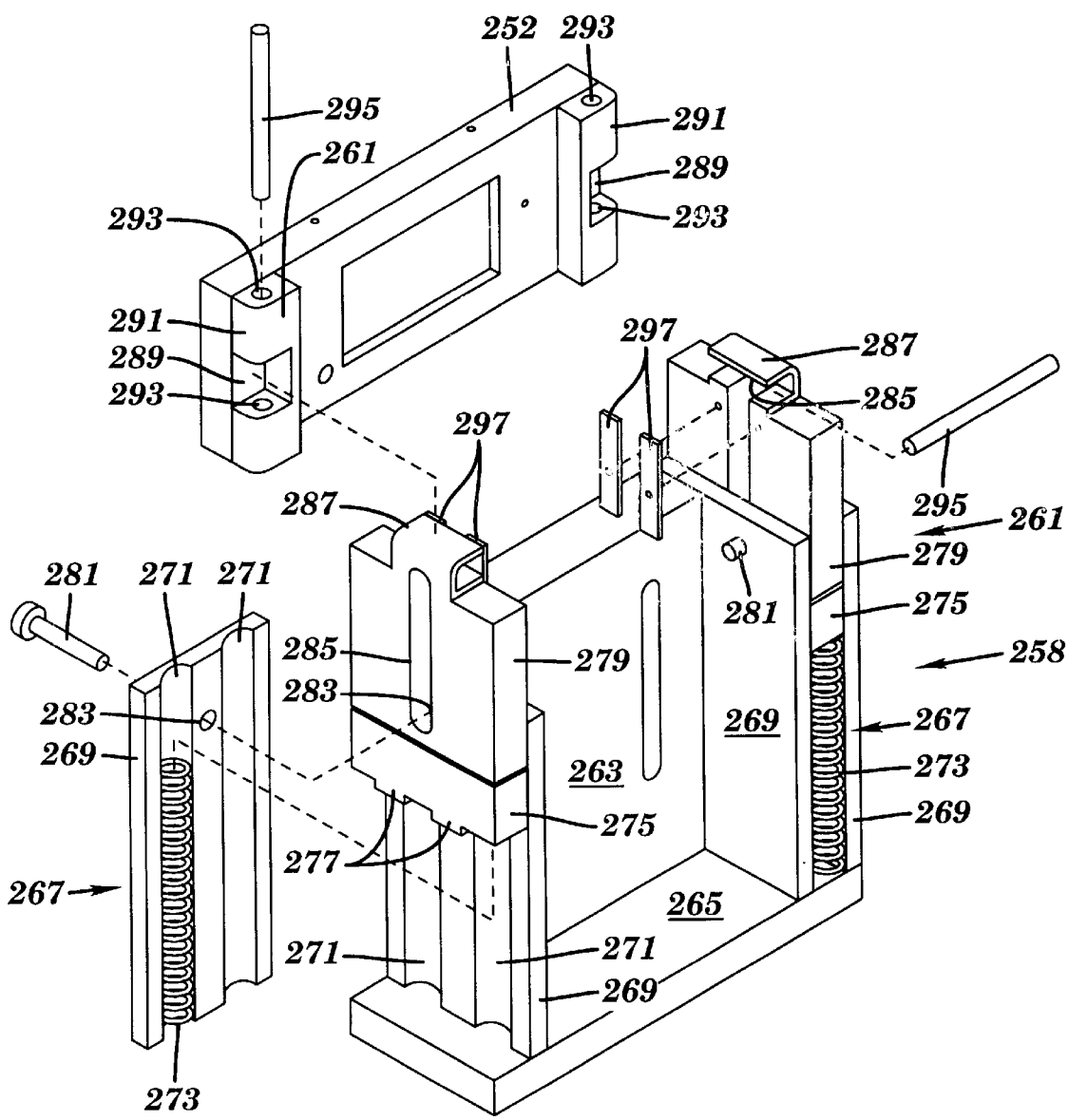
FIG. 8 is an exploded perspective view of the FIG. 7 embodiment.

FIGS. 7 and 8 show an alternative preferred embodiment of a mounting system 258. This system includes a detection head housing 252 similar to the above-described housing 52 relative to how the EMAT is mounted. A detection head 40 would be mounted to housing 252 as described above relative to housing 52. In this embodiment, housing 252 is pivotally coupled to a shock absorbing pivot frame 261 that allows pivoting of a detection head about a first axis parallel to a wheel axis, about a second axis substantially perpendicular to the first axis (or substantially parallel the rail). Mounting system 258 also allows some vertical translation.

Shock absorbing frame 261 includes a mounting plate 263 for mounting frame 261 to an aperture in a rail 34A, 34B. Mounting plate 263 is coupled to a bottom plate 265 and a pair of upstanding motion supports 267. Each motion support 267 includes a pair of parallel plates 269. Plates 269 each include two rounded grooves 271. Each groove 271, when plates 269 are mounted to bottom plate 265 and mounting plate 263, are opposite a facing groove 271 of an opposing plate 269. Each pair of facing grooves form a guide surface for compressibly constraining a compression spring 273 therein.

Positioned atop springs 273 and also constrained by plates 269, is a floating member 275. As shown in FIG. 8, each floating member 275 includes a pair of projections 277 that are sized to seat within a top ring of a compression spring 273.

A detection head mount 279 sits atop each floating member and is contained between plates 269 by a bolt 281, or other appropriate fastener, that extends through aligned apertures 283 in plates 269 and a slot 285 in head mount 279. Each head mount 279 includes a pivot seat 287 on a top surface thereof.

Detection head housing 252 includes a pair of pivot sections 291 having openings 289 therein for receiving pivot seats 287. Aligned apertures 293 in pivot sections 291 and pivot seats 287 receive pivot pins 295 therein to allow pivoting motion of detection head housing 252 relative to head mounts 279. Each pivot pin 295 is retained in pivot seats 287 by a pair of leaf springs 297 coupled to head mounts 279.

Plates 263, 265, 269 may be coupled in any known reliable fashion. For instance, they may be welded or bolted together.

Mounting system 258 allows pivotal motion of detection head housing 252 about an axis substantially parallel the wheel supporting surface 15 by head mounts 279 pivoting about bolts 281 against the bias of compression springs 273. Pivoting about another axis (or axes) substantially perpendicular to the before-mentioned axis is provided by pivoting about pins 295. As head mounts 279 move vertically between plates 269 against the bias of compression springs 273, vertical translation is also provided. Leaf springs 297 allow limited movement of pins 295 into and out of pivot seats 287 to provide additional flexure of the system. System 258 provides another mechanism capable of assuring adequate contact time with a passing wheel.

Figure 9:
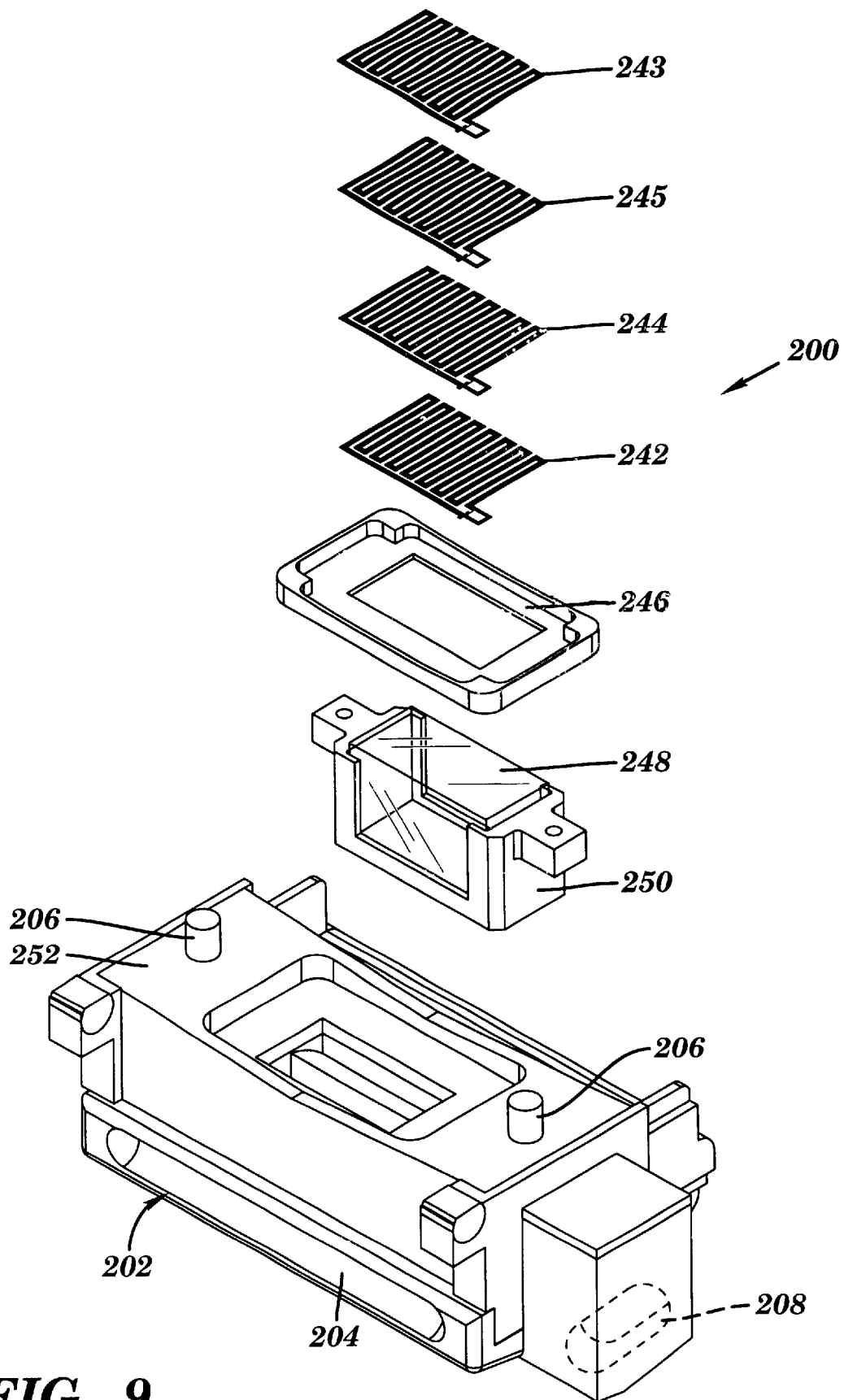
FIG. 9 is an exploded perspective view of a hand held wheel inspection system and a transducer therefor.
Figure 10:
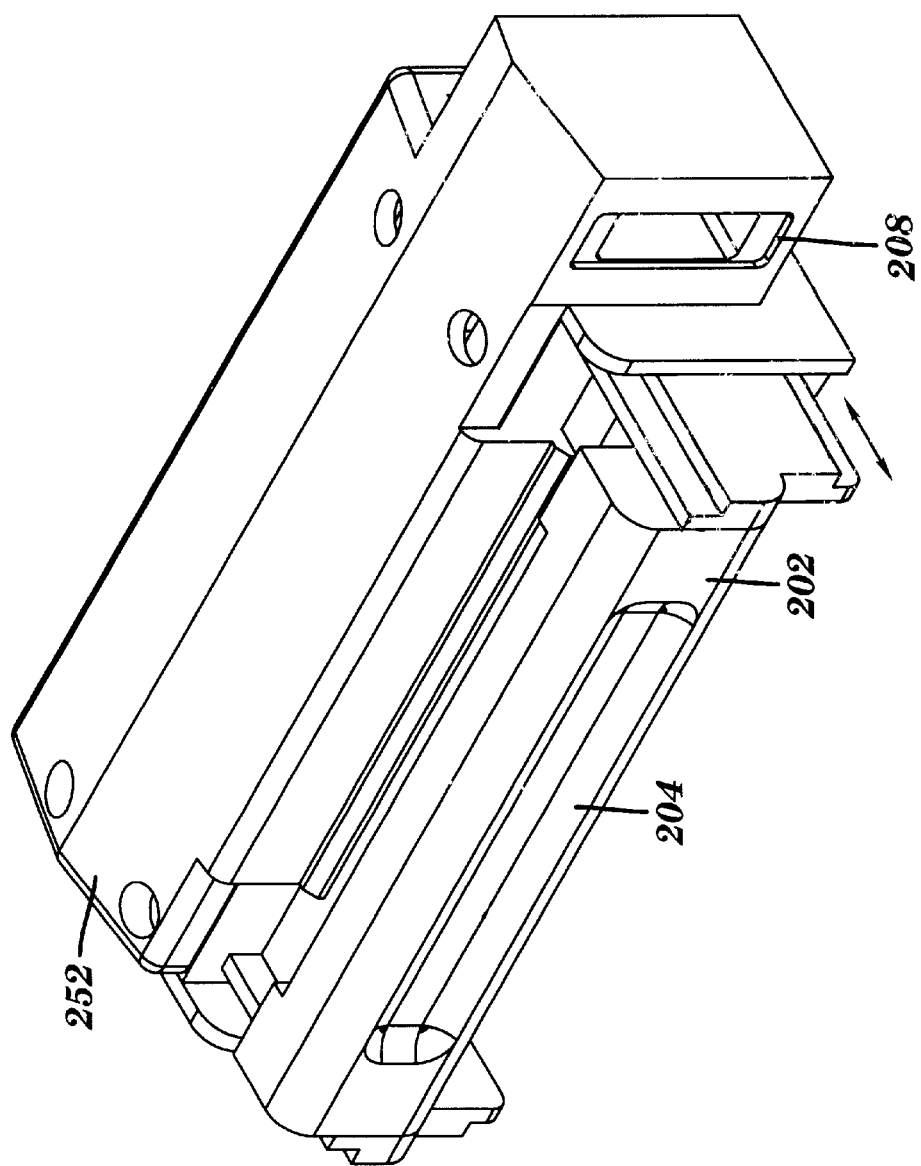
FIG. 10 is a perspective view of the hand held wheel inspection system of FIG. 9.

Referring to FIGS. 9 and 10, another preferred embodiment of the wheel inspection system in the form of a portable unit 200 is disclosed. A portable unit 200 may be placed in contact with a wheel periphery when the wheel is not in motion. This portable unit 200 includes a hand held detection head housing 252 for mounting transducer components such as transmit coil(s) 242, 245 receiving coil(s) 243, 244, removable tranducer assembly 246, magnet 248 and removable magnet assembly 250. Transducer components are mounted and used identically as described above, except magnet assembly 250 is not retractable.

As shown in FIG. 10, portable unit 200 may incorporate a hand-operated removal mechanism 202 that assists in removing unit 200 from a wheel under the attractive influence of magnet 248. Hand mechanism 202 includes a slidable handle 204 that when depressed, as shown in FIG. 9, activates at least one and preferably two plungers 206 on the wheel engaging face of housing 252. Plungers 206 contact the wheel to separate portable unit 200 from the wheel. Handle 204 may be directly connected to plungers 206 or, preferably, may be cammed to move plungers 206 to the actuated position. As shown in FIG. 10, a connector port 208 may also be provided for coupling a portable data acquisition unit and a portable computer control unit (not shown) to unit 200.

Figure 11:
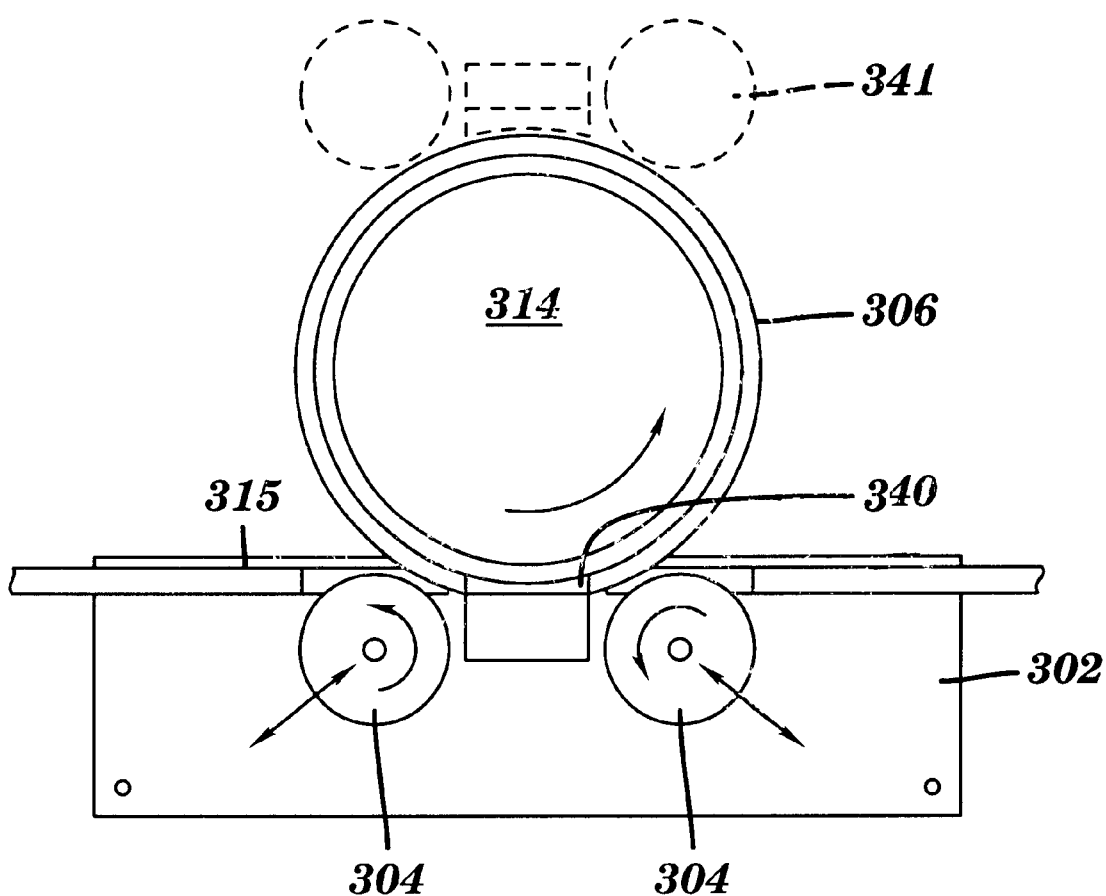
FIG. 11 is a side view of an alternative preferred embodiment.

Another alternative embodiment, shown in FIG. 11, may incorporate any of the above detection head mounting systems and electronic systems to inspect a wheel 314 in a stand-alone or vehicular mounted structure 302. This type of system is typically associated with a wheel handling system or surface re-machining operation, such as but not limited to, a wheel lathe. The system has a support surface 315 where the wheel 314 to be inspected is placed. Wheel 314 is brought in proximity of detection head 340 and a set of support rollers 304, movably fixed within support surface 315, contact wheel 314 on either side of detection head 340. Rollers 304 are movable to to elevate and support wheel 314 and cause wheel 14 to rotate over detection head 340. Using the above described detection head 340, it is possible to make a detailed interrogation of the wheel tread, flange, and plate 306 for any defects. With regard to detecting defects in plate 306 of a non-vehicular mounted wheel 314, a configuration may be made up of several detection heads 340, 341 located at various points along the circumference of wheel 314 directing ultrasonic energy through plate 306 as wheel 314 is rotated in proximity to the detection heads.

In operation in a roll-by environment, as shown in FIG. 1B, a wheel 14 rolls along a wheel support surface 15 such as a rail 34A, 34B. As discussed above, an approach sensor 38 indicates the approach of wheel 14 to wheel inspection system 10, and computer control unit 18 and data acquisition unit 28 are activated upon wheel 14 reaching sensors 16. Data acquisition unit 28 monitors signals received from electromagnetic acoustic transducer 28 and determines defects. The received signals, however, can be damaged by environmental noise. Environmental noise can be created by a variety of sources. One example of environmental noise is the signal alteration created by a locomotive traction system. Other machinery working adjacent a detection head, e.g., a lathe head, may also create noise. To improve accuracy of the system, a preferred embodiment of the invention includes a noise removing system.

The noise removing system may take a variety of forms, some of which can be used alone or in combination with others. In one preferred embodiment, the noise removing system is provided as a plurality of physically displaced receiving coils 43, 44 within a single EMAT 12A–D. In other words, as shown in FIG. 5, more than one receiving coil 43, 44 can be provided in removable transducer assembly 46. In the preferred embodiment, the additional receiving coil(s) 43 and transmit coils 42 will be physically displaced along an axis of the same rail to prevent interference. While it is possible to also physically displace receiving coil(s) 43, 44 to prevent interference, it is preferred to provide the additional receiving coil(s) 43 with a different configuration, e.g., number of coils, than receiving coil 44 and not physically displace the additional receiving coil(s) 43 relative to first receiving coil 44. In this setting, one receiving coil 44 is used to receive overall data and another receiving coil(s) 43 is used to receive only noise data. The resulting signals can then be subtracted from one another in data acquisition unit 28 or computer control unit 18 to leave an accurate signature of wheel defects only. It should be recognized that more than two receiving coils 43, 44 are also possible and that a number of noise problems can similarly be removed to acquire an accurate wheel signature. Additional transmit coil(s) 45 may also be provided, as necessary.

In another preferred embodiment of the noise removing system, referring to FIG. 1B, a system of simultaneous wheel inspection and noise determination can be set up between a pair of EMATs 12A–D. In this setting, a receiving coil 44 in one EMAT 12A, located on a first rail 34A of a multiple rail track, is used to obtain a wheel 14 defect signal (i.e., a signal without any environmental correction) while a receiving coil 44 in another EMAT 12B, located on a second rail 34B of the multiple rail track, is used to determine a noise signal. This can be provided in a number of ways, for instance, by having receiving coil 44 in different EMATS 12A–D have different configurations, e.g., width of coils. The resulting signals can then be subtracted from one another in data acquisition unit 28 or computer control unit 18 to leave an accurate signature of wheel defects only. As shown in FIG. 1B, it is preferred that EMATs 12A–D are not directly opposite one another on opposing rails 34A, 34B. This set up assures that when one EMAT 12A–D measures for wheel defects, there is always another EMAT 12A–D without a wheel upon it and capable of measuring noise only.

In the above described preferred embodiments, a switching device 29, shown in FIG. 1A, is provided to selectively switch between which receiving coil's (43 or 44) output is being input to data acquisition unit 28. For instance, when receiving coils 43, 44 are physically displaced along an axis of the same rail, the switching device is employed to sequentially receive input from receiving coils 43, 44.

Another preferred embodiment of the noise removing system includes a matched filter 31, shown in FIG. 1A. Matched filter 31 is configured to match the amplitude frequency response corresponding to a frequency spectrum of radio frequency generator 22. Accordingly, when matched filter 31 is applied to an overall data signal, noise can be removed, leaving an accurate signature of wheel defects only. While matched filter 31 is shown in data acquisition unit 28, it should be recognized that it can be located in a variety of positions within system 10.

Other mechanisms of providing a noise removing system include: having radio frequency generator 22 produce a phase modulated output such that a signature may be applied to the transmitted signal providing a means of identifying the desired signal upon reception; having data acquisition unit 18 monitor multiple data frames to statistically improve a signal to noise ratio, e.g., by statistical averaging; and/or having data acquisition unit 18 employ neural network techniques to train data acquisition unit 18 based upon known defect and non-defect signals. It should be recognized that while certain preferred embodiments have been described separately, that the noise removal system may incorporate one of the preferred embodiments or a number of them. For instance, one could use two receiving coils 43, 44 and also use statistical averaging and/or neural network techniques.

With further reference to FIG. 5B and EMATs 12A–D, having more than one EMAT 12A–D on a single rail 34A, 34B also functions to assure that a complete evaluation of a wheel is possible. In particular, it is estimated that each EMAT 12A–D is capable of evaluating everything except about 20 percent of the circumference of wheel 14 during an individual data frame. These "blind spots" are caused by signal cancellations at the top of each wheel 14, and by the masking of defect signals adjacent each EMAT 12A–D due to the transmit pulse induced overload recovery time of the receive system. These "blind spots" are normally not a problem because most defects are in the form of multiple defects and, therefore, readily detected. Nonetheless, for complete inspection, placing a pair of EMATs 12A, 12D or 12B, 12C about some fraction of a circumference of wheel 14 apart assures that the entire wheel is inspected.

Turning to data analysis conducted by data acquisition unit 28, wheel inspection system 10 automatically separates and classifies defective wheels from undamaged wheels. Complications in obtaining useful defect signals from wheel cracks arise from several sources including external noise from locomotive traction power, blind spots in sensor response, variability in sensor to wheel coupling, and variable signal conduction quality within the wheel. The invention may use several different signal processing algorithms including, for example, neural networks, data correlation, and wavelet analysis of wheel signatures to remove the above-described complications.

Neural networks used with the invention will include a number of layers of learned relationships about signal data and related defects. For instance, a feed forward neural network will include a number of layers of learned relationships about signal data and can "feed forward" to higher layers of knowledge. Hence, data analysis can use prior experience to be more accurate regarding the type of defects present. In order to use neural networks, preferably a feed forward neural network 114 in data acquisition unit 28 is trained using useful signatures extracted from the ultrasonic signal waveform obtained by wheel inspection system 10. A neural network 114 is built by taking raw ultrasonic signals returned from wheels having known defects to build the network. The signals used are filtered, processed through a Hilbert Transform, and normalized or adjusted for wheel diameter to create neural network training signals. The wheel diameter can either be externally inputted or derived by wave round trip time data, i.e., by the time it takes for a round trip of a wave through a wheel. A Hilbert Transform is a software method of providing envelop detection as opposed to using a hardware method of envelop detection. Another signature that can be used to train a neural network 114 includes a signal zero crossing count of the filtered signature i.e., a count of a given signal cycle through zero as it passes from positive and negative values, and vice versa. When a properly trained neural network 114 is presented with a signature from an unknown wheel, the neural network will automatically determine if the presented wheel is flawed or not. Other types of signatures and different types of neural network configurations, e.g. back-propagation, are also possible to identify bad wheels in a manner similar to what is stated above.

In a preferred embodiment, a number of neural networks 114 and a number of sensors are used to eliminate blind spots and allow more accurate data analysis. In this setting, it is preferred to use an odd number of sensors spaced from one another by a distance equal to the circumference of the wheel divided by the number of sensors. For instance, as shown in FIG. 1A, three sensors 12A–D, 112A, 112B may be used with spacing equal to 1/3 of the wheel 14 circumference. Although not shown for clarity sake, sensors 112A and 112B are connected to computer control unit 18, RF generator 22 and data acquisition unit 28 identically as sensors 12A–D. Signals from each sensor are digitized, filtered and envelope detected. Further processing breaks the signals into regions delimited by the round trip pulse. Each region is normalized, or adjusted, in amplitude by an amount related to the ratio of the current to the previous round trip pulse amplitude. Time series averaging is then applied to the ensemble of regions. Such processing serves to attenuate noise that is not correlated to the round trip time. After the processing described, the resultant signal is further divided into a number of equally spaced time regions within the round trip interval. The resultant set of signals is preferentially applied to a neural network 114 of the feed forward type that has been previously trained to recognize the characteristics of the round trip and defect signals. The processed outputs of each sensor are processed by identically trained neural networks, e.g., for neural network for each sensor. The output of each network takes on one of states: 1) no defect, 2) single defect, 3) multiple defects, 4) unrecognized. The outputs from the networks can be processed by a fuzzy logic network 116 in data acquisition unit 28 to generate a summary signal reflecting the best estimate of the condition of the wheel. In another embodiment of the invention, the plurality of neural networks 114 can be replaced by a single network that produces the final wheel defect signal.

Wheel inspection system 10 may also use analysis of data correlation of the multiple round trips through a wheel 14 that the ultrasonic energy takes every time a wheel 14 goes over a detection head 40. Analyzing the data correlation between multiple round trip data, can be used to eliminate erroneous data sets. Furthermore, additional round trip data can be added after phase correction to arrive at a single round trip representation with much larger amplitude than possible with any single round trip data.

Another mechanism that can be employed to discard erroneous data and help in understanding the wheel defect related echos is using an independently arrived at approximate wheel diameter measurement. The velocity of sound is known to travel in the wheel at approximately 0.125 inches per micro-second. Therefore, knowing the diameter of a wheel 14, one can establish where round trip echos should appear in received time amplitude waveform. If round trip echos are missing at a calculated time location or echos with larger amplitude appear before the round trip echos, one can determine whether there is a lack of good detector contact, a wheel anomaly, or a defect in wheel 14. As will be recognized by those skilled in the art, other types of time-amplitude analysis can be used to identify bad wheels in a manner similar to what is stated above.

Another mechanism of defect detection is wavelet analysis of time-amplitude-frequency. This form of analysis can be used to recognize certain defects, e.g. thermal defects, that show characteristic waveforms.

It should be recognized that the above-described data analysis methods may be executed through the use of computer software techniques or by the use of electronic circuits or any combination thereof.

While this invention has been described in conjunction with the specific embodiments outlined above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention as defined in the following claims.

One example, shown in FIG. 1B, is that the entire system 10 may be remotely accessed via wireless communication 3.

Also, while a sensor area of detection head 40 has been shown in contact with a wheel 14, detection head 40 may also operate while not in contact with wheel 14. This can be made possible in a number of ways. For example, by increasing the magnetic field of the EMAT; substantially increasing the transmit energy; increasing the receive amplification; and/or using different EMAT configurations. Non-contact operation is particularly advantageous when the system is incorporated into the non-roll-by wheel inspection system. One example is when wheel 14 is rotated while in proximity of a detection head 40 when in a wheel handling/machining device such as, but not limited to, a wheel lathe.

Another modification is that the defect detection system may use, rather than the described EMAT 12A–D, alternate means of generating ultrasonic energy, such as but not limited to, the use of a pulsed laser.

We claim:

1. A wheel inspection system comprising:
    at least one electromagnetic acoustic transducer having a transmit coil to propagate an ultrasonic wave into a wheel and a receiving coil to receiving an ultrasonic surface wave from the wheel;
    a radio frequency generator for exciting the electromagnetic acoustic transducer and producing an ultrasonic wave in the wheel;
    a computer control unit connected to and communicating with the radio frequency generator and the electromagnetic acoustic transducer;
    a data acquisition unit connected to and in communication with the computer control unit and the electromagnetic acoustic transducer for determining and analyzing defects in the wheel; and
    a noise removing system to remove noise from the data.

2. The system of claim 1, wherein the noise removing system includes a plurality of receiving coils, one coil of which receives overall data and another coil of which receives noise data.

3. The system of claim 2, wherein a first receiving coil is located on a first rail of a multiple rail track that supports a wheel and a second receiving coil is located on a second rail of the multiple rail track.

4. The system of claim 2, further comprising a switching device to selectively switch between which receiving coil output is being input to the data acquisition unit.

5. The system of claim 2, wherein the receiving coils are placed along an axis of the same rail and a switching device selectively switches between which receiving coil output is being input to the data acquisition unit.

6. The system of claim 1, wherein the noise removing system includes a matched filter having an amplitude frequency response corresponding to a frequency spectrum of the radio frequency generator.

7. The system of claim 1, wherein the noise removing system includes the radio frequency generator producing a phase modulated output.

8. The system of claim 1, wherein noise removing system includes the data acquisition unit monitoring multiple data frames to statistically improve a signal to noise ratio.

9. The system of claim 1, wherein the radio frequency generator produces a plurality of frequency components in an output thereof to create a series of ultrasonic waves that travel in varying depths within the wheel.

10. The system of claim 1, further comprising a plurality of transmit and receiving coils of differing configurations to create a first ultrasonic wave traveling substantially at a tread surface of the wheel and a second ultrasonic wave traveling substantially at a flange surface of the wheel.

11. The system of claim 1, wherein the data acquisition unit further determines a wheel diameter.

12. The system of claim 1, wherein the radio frequency generator includes a bridge network to couple multiple radio frequency sources to an output coil to increase the transmitted power.

13. The system of claim 1, wherein the electromagnetic acoustic transducer is mounted in a hand-held assembly.

14. The system of claim 13, wherein the hand-held assembly includes a connector port to communicate with a portable computer control unit and the data acquisition unit.

15. The system of claim 13, further comprising a removal device for removing the hand-held assembly from a wheel.

16. The system of claim 1, further comprising a detection head for the electromagnetic acoustic transducer, the detection head including:
    a housing for holding transducer components, the housing including a transducer pocket and a magnet pocket;
    a removable magnet assembly for removably mounting a magnet to the magnet pocket; and
    a removable transducer assembly for removably mounting a coil assembly of the transducer to the transducer pocket.

17. The system of claim 16, further comprising a removal device for removing the housing from a wheel when the detection head is hand held.

18. The system of claim 1, wherein the electromagnetic acoustic transducer (EMAT) includes at least three EMATs for receiving signals sent through a wheel; and the data acquisition unit is connected to and in communication with each EMAT, the data acquisition unit including a neural network, to determine the presence of defects in the wheel, for each EMAT.

19. The system of claim 18, wherein the at least three EMATs includes an odd number of EMATs.

20. The system of claim 18, wherein output from the neural network is processed by a fuzzy logic network.

21. The system of claim 1, further comprising means for pivotally mounting the electromagnetic acoustic transducer to a wheel supporting surface such that the EMAT may pivot about at least two axes.

22. The system of claim 21, wherein the means for pivotally mounting is retractable relative to the wheel support surface.

23. A detection head for an electromagnetic acoustic transducer wheel inspection system, the detection head comprising:

a housing for holding transducer components, the housing including a transducer pocket and a magnet pocket;

a removable magnet assembly for removably mounting a magnet to the magnet pocket; and a removable transducer assembly for removably mounting a coil assembly of the transducer to the transducer pocket.

24. The detection head of claim 23, further comprising a removal device for removing the housing from a wheel when the detection head is hand held.

* * * * *